United States Patent
Liu et al.

(10) Patent No.: US 6,299,866 B1
(45) Date of Patent: Oct. 9, 2001

(54) WATER-BASED, HAIR CARE PRODUCTS CONTAINING HOMOGENEOUS TERPOLYMERS HAVING BOTH HAIR STYLING AND CONDITIONING PROPERTIES

(75) Inventors: Kou-Chang Liu, Wayne; Robert B. Login, Oakland; Yakir Reuven, West Orange, all of NJ (US); Janice Kay Bees, Libertyville, IL (US)

(73) Assignees: ISP Investments Inc., Wilmington, DE (US); Helen Curtis, Inc. a part interest, Chicago, IL (US)

( * ) Notice: Subject to any disclaimer, the term of this patent is extended or adjusted under 35 U.S.C. 154(b) by 0 days.

(21) Appl. No.: 08/365,720

(22) Filed: Dec. 28, 1994

(51) Int. Cl.$^7$ ...................................................... A61K 7/06
(52) U.S. Cl. .................................. 424/70.15; 424/70.16; 424/70.17; 424/70.11

(58) Field of Search .............................. 424/40.15, 40.16, 424/40.17, 40.11

(56) References Cited

U.S. PATENT DOCUMENTS

| | | | | |
|---|---|---|---|---|
| 4,324,780 | * | 4/1982 | Jacquet | 424/47 |
| 4,719,099 | * | 1/1988 | Grollier | 424/47 |
| 4,865,838 | * | 9/1989 | Gross | 424/47 |
| 5,182,098 | * | 1/1993 | Kopolow | 424/47 |
| 5,221,531 | * | 6/1993 | Kopolow | 424/71 |
| 5,326,555 | * | 7/1994 | Hardy | 424/71 |

* cited by examiner

Primary Examiner—Thurman K. Page
Assistant Examiner—P. E. McQueeney
(74) Attorney, Agent, or Firm—Walter Katz; William J. Davis; Marilyn J. Maue

(57) ABSTRACT

Water-based, hair care products containing homogeneous terpolymers having both hair styling and conditioning properties is described.

14 Claims, 2 Drawing Sheets

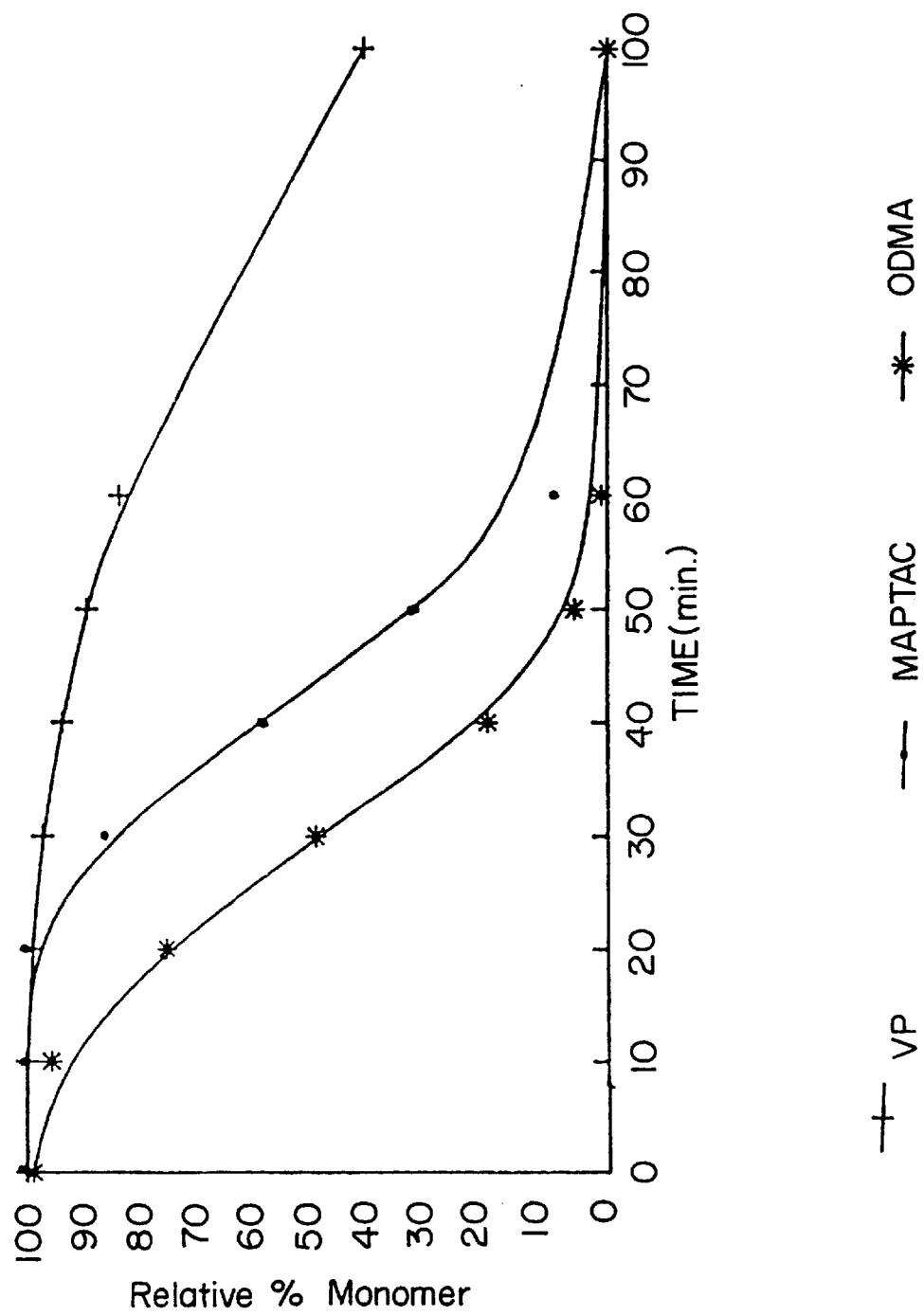

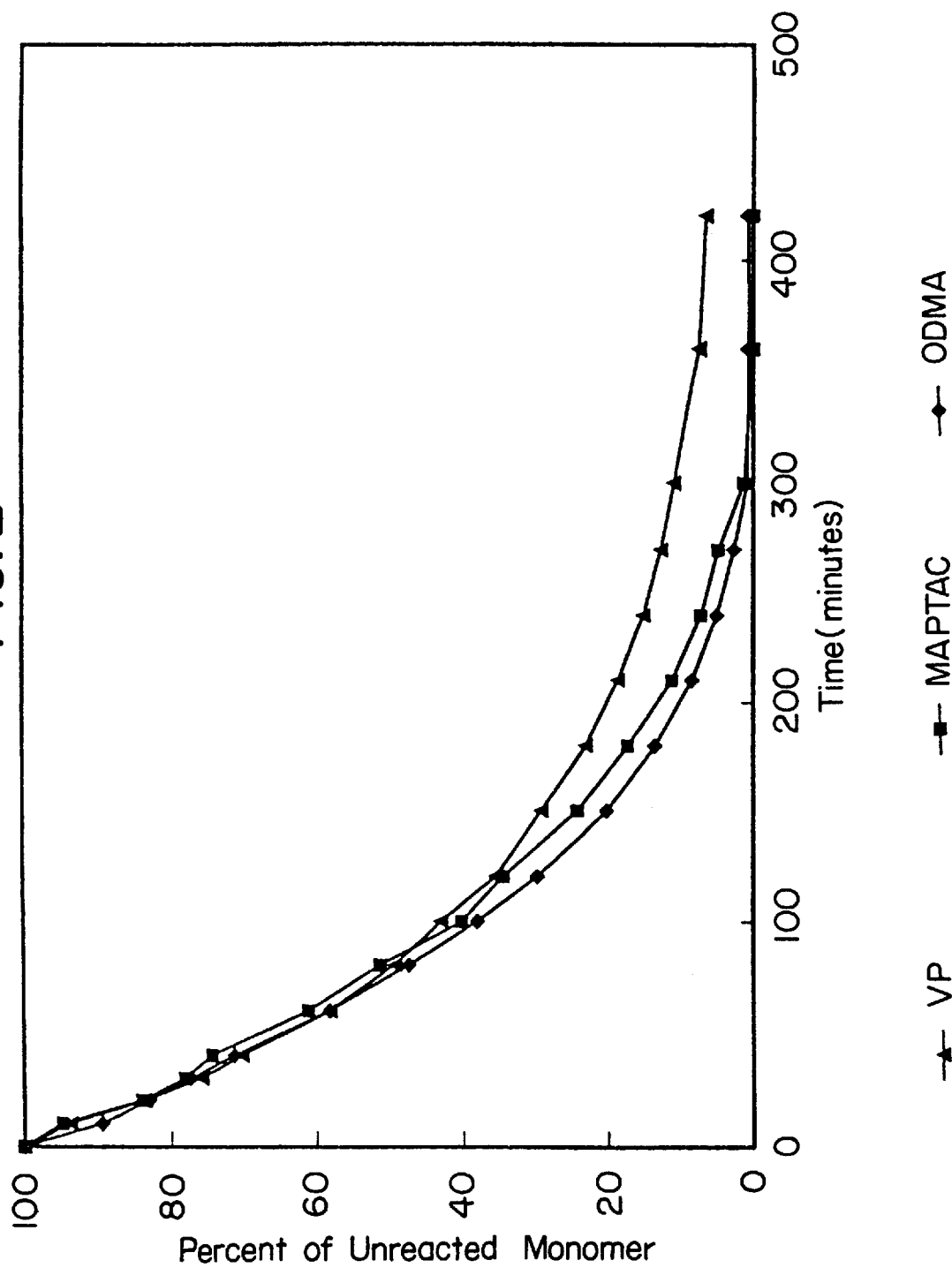

WATER-BASED, HAIR CARE PRODUCTS CONTAINING HOMOGENEOUS TERPOLYMERS HAVING BOTH HAIR STYLING AND CONDITIONING PROPERTIES

BACKGROUND OF THE INVENTION

1. Field of the Invention

This invention relates to hair care products, and, particularly to hair care compositions which provide both hair styling and conditioning for the user, characterized by the presence therein of a homogeneous terpolymer of predetermined composition.

2. Description of the Prior Art

Multifunctional hair care products such as hair styling and conditioning compositions have become popular with the public. Such compositions have been made available in the form of gels, lotions, sprays, mousses and glazes, which can be removed after use either immediately, for example, in the so-called "rinse-off" application, where, however, some of the composition remains on the hair after treatment with water, or by the "leave-on" application, where some time later, a majority of the composition is removed with water, or all of it is removed with shampoo.

Hair styling and conditioning compositions in the form of gels are provided by the inclusion of a suitable amount of a gelling agent, generally to provide a 7–10,000 cps formulation which can be dispensed by hand or by pump application. Lotion hair care products are hydroalcoholic (3–15%) formulations which can be applied by hand. Sprays are formulations for application by pump action. Mousses are compositions which can be dispensed easily and conveniently from an aerosol can as a pressure sensitive foam. Glazes are thin gel formulations.

Mousse and gel hair styling compositions have become particularly popular with the public. A mousse gives an appearance of penetration of the hair as the foam collapses and has ingredients that perform functions that are needed for the improved styling of hair. In particular, these ingredients add body to the hair, thereby making it appear fuller on the head of the user, and enhance the combability of the hair in order to make it more manageable. In a mousse, some of the collapsed foam may be designed to be combed out of the hair during the process of styling.

Several synthetic polymers containing vinyl lactams are presently being used in cosmetic formulations, particularly in hair care products, to contribute body and set retention and conditioning to such products.

Representative of the art in this field are the following U.S. Pat. Nos. 3,914,403; 3,954,960; 4,057,533; 4,210,161; 4,586,518; 4,753,793; 4,764,363; 4,834,968; 4,842,850; 4,902,499; 4,906,459; 4,923,694; 4,963,348; 4,983,377; 5,011,895 and 5,015,708; and WO 91/15186; WO 91/15185; EPO 0412704A2; EPO 0412707A1; and JP 57126409.

These synthetic polymers generally were made by a "one-pot" polymerization process in which selected amounts of the several monomers were reacted together. The composition of the thus-formed polymer was considered as being the same as the composition of the charged monomers. Unfortunately, such conventional polymerization processes can provide only a mixture of polymers of various compositions, and, additionally, unwanted homopolymers and undesired copolymers of one or more of such monomers.

Commercial hair care products contain ethanol as the organic solvent for the film-forming hair fixative resin. However, ethanol is disfavored because it is a volatile organic compound (VOC) which can pollute the air; also it can give beauticians upper respiratory infections and irritations of the nose and skin. Furthermore such organic solvents can damage the hair; and it is a flammable substance. Accordingly, low VOC hair care products which is reduced or alcohol-free, is desired in the hair care industry. Particularly sought after are hair care polymers which are also suitable for use in water-based, multifunctional hair care products, and, which can perform the dual functions of styling and conditioning effectively.

Representative of the art in this field are the following U.S. Pat. Nos. 3,914,403; 3,954,960; 4,057,533; 4,210,161; 4,586,518; 4,753,793; 4,764,363; 4,834,968; 4,842,850; 4,902,499; 4,906,459; 4,923,694; 4,963,348; 4,983,377; 5,011,895 and 5,015,708; and WO 91/15186; WO 91/15185; EPO 0412704A2; EPO 0412707A1; and JP 57126409.

Accordingly, it is an object of this invention to provide a water-based, multifunctional hair care product containing a homogeneous polymer of predetermined composition made by homogeneous polymerization of several monomers having differing reactivity ratios.

A further object herein is to provide such hair care products in the form of gels, lotions, sprays, mousses and glazes which can be removed after use either immediately or some time thereafter.

Another object of the invention is to provide multifunctional hair styling and conditioning compositions containing homogeneous polymers of a plurality of monomers, including a vinyl lactam, preferably vinyl pyrrolidone (VP), a quaternary amino monomer, preferably 3-methacrylamidopropyl trimethylammonium chloride (MAPTAC), and a hydrophobic monomer, preferably a $C_4$–$C_{32}$ alkyl methacrylate, most preferably octadecyl methacrylate (ODMA).

Yet another object of this invention is to provide a water-based, rinse-off, hair care product which can provide both hair styling and conditioning functions, containing a homogeneous terpolymer of predetermined composition, which can be deposited onto hair as a clear film.

A particular object herein is to provide a hair care product including a positively charged fixative homogeneous terpolymer which has a predetermined ratio of hydrophilic-to-hydrophobic monomers therein, with predominately hydrophilic components, and which can be formulated into a 100% water-based hair care product.

Among the other objects herein is to provide dual hair styling and conditioning compositions in which the polymers in such composition are made by polymerizing a plurality of monomers while adjusting the feeding rates for the faster reacting monomers relative to the precharged slowest reacting monomer so that all the monomers ca react at substantially the same rate during the polymerization.

These and other objects and features of the invention will be made apparent from the following more particular description of the invention.

SUMMARY OF THE INVENTION

The water-based, hair care product of the invention contains a homogeneous terpolymer of predetermined composition having both hair styling and conditioning properties.

The homogeneous terpolymer of the invention comprises, by weight, about 55–99%, preferably 65–95%, of a vinyl lactam, preferably vinyl pyrrolidone (VP), about 0.5–49%, preferably 5–25%, of a quaternary amino monomer, e.g., (3-methacrylamidopropyl) trimethylammonium chloride (MAPTAC), and about 0.5–49%, preferably 1–25%, of a hydrophobic monomer, having the formula RMA, where R is $C_4$–$C_{32}$ alkyl, preferably $c_{12}$–$C_{32}$ alkyl, and, most preferably, octadecyl methacrylate (ODMA).

The homogeneous terpolymer suitably is present in the hair care product in an amount of about 0.2–20%, preferably 1–10%, most preferably 2–8%, by weight of the product. During use, the terpolymer of the invention furnishes a positive charge (MAPTAC) and a predetermined blend of hydrophilic components (VP/MAPTAC) to its hydrophobic component (RMA), to provide both styling and conditioning functions. Such products are readily adsorbed onto the negatively charged hair of the user, but can be easily washed off with shampoo after use.

The benefits of this invention are:

(1) Greater water solubility of the polymer because of uniform incorporation of water soluble monomers therein, e.g. vinyl pyrrolidone.

(2) Improved polymer adsorption onto hair due to the presence of quaternary salts as anchoring groups uniformly distributed among the polymer chains.

(3) Enhanced clarity of terpolymer composition, and films cast from them.

The homogeneous polymerization process of the invention includes precharging VP, and solvent, and introducing the MAPTAC and ODMA monomers incrementally at rates corresponding to the rate of disappearance of VP, over a given period of time.

IN THE DRAWINGS

FIG. 1 is a graphical representation of a conventional non-homogeneous ("one-pot") polymerization process for making a terpolymer of vinylpyrrolidone (VP), 3-methacrylamidopropyl trimethylammonium chloride (MAPTAC), and octadecyl methacrylate (ODMA) monomers from precharged amounts of the monomers. The relative monomer content of each monomer remaining during the polymerization is plotted vs. time.

FIG. 2 is a graphical representation of the homogeneous process of the invention for making the same terpolymer.

DETAILED DESCRIPTION OF THE INVENTION

A. Terpolymer of Invention

1. Hydrophilic Monomers (a) Lactam Monomer

Vinylpyrrolidone is the most preferred vinyl lactam.

The vinyl lactam monomer is present in an amount of about 55–99%, and, preferably, 65–95%, by weight of the terpolymer.

(b) Quaternary Amino Acrylamide or Acrylate Monomer

The quaternary amino acrylamide or acrylate monomer in the terpolymer of the invention has the formula:

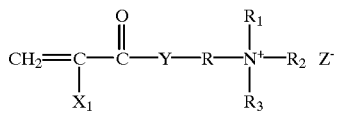

where

Y is O or —NX—;

R is $C_2$–$C_{20}$ alkyl or

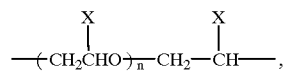

where n is 0–10,

X and $X_1$ are independently H, or $C_1$ to $C_8$ alkyl;

$R_1$, $R_2$ and $R_3$ are independently $C_1$–$C_4$ alkyl; and

Z is a halide, sulfate or sulfonate.

Suitable examples of amino acrylamides, acrylates, methacrylamides, or methacrylates which are employed as monomers in the terpolymer of the invention include quaternized salts of N-[12-(dimethylamino)dodecyl] methacrylamide or methacrylate; N-[18-(dimethylamino) octadecyl]methacrylamide or methacrylate; N-[8-(dimethylamino)octyl]methacrylamide or methacrylate; N-[7-(dimethylamino)heptyl]acrylamide or acrylate; N-[14-(dimethylamino)tetradecyl]acrylamide or acrylate; N-[3-(dimethylamino)propyl]methacrylamide or methacrylate; N-[3-(diethylamino)propyl]acrylamide or acrylate; N-[4-(dipropylamino)butyl]methacrylamide or methacrylate; N-[3-(methyl butyl amino)propyl]acrylamide or acrylate; N-{2-[3-(dimethylamino)propyl]ethyl}acrylamide or acrylate; and N-{4-[4-(diethylamino)butyl]butyl}acrylamide or acrylate.

Of the above group, the N-[(dimethylamino)alkyl] methacrylamides or acrylamides, methacrylates and acrylates of their quaternized halide, sulfate and sulfonate salts are preferred. Of these, 2-(ethyl dimethylammonium) ethyl methacrylate sulfate; (3-methacrylamidopropyl) trimethylammonium chloride (MAPTAC); (3-acrylamido-3-methylbutyl)propyl trimethylammonium bromide; (3-methacrylamido-3-ethyl-butyl)propyl trimethylammonium chloride; (4-acrylamido-n-methylbutyl)propyl trimethylammonium chloride; and (3-methacrylamidopropyl) ethyl dimethylammonium ethyl sulfate, or a mixture thereof, are most preferred. Where the quaternized amino acrylamide is (3-methacrylamidopropyl)trimethylammonium chloride, the formula is represented by X and $X_1$ being $CH_3$; Y being NH; R being $C_3$ alkyl; $R_1$, $R_2$ and $R_3$ being methyl; and Z being chloride.

The quaternary amino monomer suitably is present in the terpolymer in an amount of about 0.5–49%, and, preferably 1–25%, by weight of the terpolymer.

The vinyl lactam and quaternary amino acrylamide or acrylate monomers constitute the hydrophilic portion of the terpolymer of the invention.

2. Hydrophobic Monomer

The hydrophobic monomer in the terpolymer of the invention suitably has the formula: RMA where R is a $C_4$–$C_{32}$ alkyl, preferably $C_{12}$–$C_{32}$ alkyl, or a mixture thereof; and MA is an acrylate, methacrylate, acrylamide or methacrylamide. Suitable hydrophobic monomers include 2-ethylhexyl methacrylate, dodecyl acrylate, tetradecyl acrylate, octadecyl methacrylate (ODMA), octadecyl methacrylamide, dodecyl acrylamide and 2-ethylhexyl methacrylamide. A preferred hydrophobic monomer is octadecyl methacrylate.

The hydrophobic monomer is present in an amount of about 0.5–49%, preferably 1–25%, by weight of the terpolymer.

B. Homogeneous Polymerization

The homogeneous polymerization process of the invention is illustrated by making substantially homogeneous terpolymers of VP, MAPTAC and ODMA in a predetermined composition.

In the homogeneous process, the least reactive monomer of the terpolymer (VP) is precharged into a reactor at a suitable reaction temperature, generally about 50–80C., and preferably 55–75° C. The more reactive monomers (MAPTAC and ODMA) then are introduced incrementally into the VP-charged reactor at a rate which corresponds to the observed rate of disappearance of VP, over the period of polymerization.

The entire predetermined amount of the MAPTAC and ODMA monomers are added before substantially all the VP monomer has been consumed so that all monomers can react to form a substantially homogeneous terpolymer in a desired compositional ratio of VP:MAPTAC:ODMA. Consequently, a substantially homogeneous terpolymer is obtained whose composition approaches the nominal monomer ratio of the desired terpolymer composition and whose structure has the three individual monomeric units of the copolymer distributed substantially uniformly in a homogeneous chain along the backbone of the polymer.

The precharge in the process of the invention may include some MAPTAC and ODMA therein, generally in an amount of up to about 15% of the total amount of MAPTAC and ODMA required for a predetermined terpolymer composition without affecting the homogeneous polymerization process. However, it is still necessary that the rate of addition of MAPTAC and ODMA after any precharge be carried out at substantially the rate of disappearance of VP during polymerization.

The schedule of addition of MAPTAC and ODMA to accomplish the desired matched rate of reaction of VP is determined in the following manner.

DETERMINATION OF ADDITION SCHEDULES FOR MAPTAC AND ODMA TO FORM A HOMOGENEOUS TERPOLYMER WITH VP

A. First, a one-pot polymerization of VP, MAPTAC and ODMA monomers is carried out as follows:

EXAMPLE 1

VP (553.5 g), MAPTAC (124.5 g), ODMA (95.6 g) and ethanol (753.5 g) were charged into a 2-liter resin pot equipped with a gas inlet, a liquid inlet, a thermometer and a condenser. The pH of the solution was adjusted to about 7.5 with KOH. A stream of nitrogen then was bubbled through the solution during the reaction. The solution was gradually heated to 68° C., and 0.25 ml of Lupersol 11 as catalyst was added; then another 0.25 ml of the catalyst was added after 10 minutes; and another 6 units of 0.25 ml amount was added each 30 minutes. The reaction was carried out for an additional 3 hours.

The relative percentage amounts of residual monomers present during the course of the one-pot reaction was determined by gas chromatographic analysis after sampling the reaction mixture periodically. The analytical data obtained then was plotted as the graph of FIG. 1.

As shown in FIG. 1, the MAPTAC and ODMA monomers react much more rapidly than VP. Accordingly, after 100 minutes, for example, all the MAPTAC and ODMA monomers are consumed while residual VP monomer still is available for homopolymerization. Thus the terpolymer formed is of a composition different from the desired monomer ratios selected by the precharged amounts of the two monomers. Under these experimental conditions, the polymer product obtained is a complex mixture of a homopolymer which is polyvinylpyrrolidone, various copolymers, and a terpolymer of the several monomers of uncertain composition.

B. To form a homogeneous terpolymer, it is necessary that the curve of rate of reaction vs. time for both MAPTAC and ODMA substantially coincide or match the rate of reaction curve for VP. To accomplish this, the VP is precharged and substantially all the MAPTAC and RMA monomers are fed external to the precharge at a feeding schedule determined by analysis of the data of FIG. 1. The % MAPTAC and ODMA monomers to be fed at time t of the polymerization is determined from the Asymmetric Double Sigmoidal Distribution formula, $A_t$, below, which has four adjustable parameters, $a_1$, $a_2$, $a_3$ and $a_4$:

$$A_t = \frac{1}{1 + \exp\left[\dfrac{a_1 - \dfrac{a_2}{2} - t}{a_3}\right]} \left[1 - \frac{1}{1 + \exp\left[\dfrac{a_1 + \dfrac{a_2}{2} - t}{a_4}\right]}\right]$$

where
  t=time in minutes during copolymerization;
  $a_1$ is a parameter which determines the center of the distribution;
  $a_2$ is a parameter which affects the width of the distribution;
  $a_3$ is a parameter which determines the ascending portion of the distribution; and
  $a_4$ is a parameter which determines the descending portion of the distribution.
  % MAPTAC or ODMA to be fed at time $$t = \frac{A_t}{\sum_{t=0}^{N} A_t} \times 100$$

where
  N=time when the polymerization is completed.

To match the MAPTAC and ODMA curves to the VP curve of FIG. 1, an "initial guess" is made for the values of $a_1$, $a_2$, $a_3$ and $a_4$ for each of these monomers. Then these values are inserted into the $A_t$ formula and the % MAPTAC and ODMA to be fed at time t is calculated. The resulting % unreacted MAPTAC and ODMA during this polymerization will probably not match the % unreacted VP at the same time t. If the % unreacted MAPTAC or ODMA at time t is too large, then the value of $a_3$ (ascendancy) in the $A_t$ formula is increased, $a_4$ (descendency) is decreased, $a_1$ (center) is decreased, and $a_2$ (width) is decreased. Conversely, if the initial guess values of $a_1$ through $a_4$ give a reaction rate for MAPTAC or ODMA which is too fast, then changes in the values of $a_1$ through $a_4$ are made in a direction opposite to those discussed above.

These new values of the parameters are then used to determine a new feeding schedule. Using this feeding schedule, another polymerization is carried out, and the process of adjustment of the parameters described above is repeated.

This process is known as "interative fitting" of data to a curve. After 4 or 5 such iterative fittings, the experimental VP, MAPTAC and ODMA curves will be matched, as shown in FIG. 2 herein.

The matched curves of VP, MAPTAC and ODMA in FIG. 2 will have at least one set of values for $a_1$, $a_2$, $a_3$ and $a_4$ (the last set of the iterative fitting process) for suitable feeding of MAPTAC and ODMA over the entire period of polymerization. One such set is:

| MAPTAC | ODMA |
|---|---|
| $a_1 = 41$ | $a_1 = 56$ |
| $a_2 = 82$ | $a_2 = 90$ |
| $a_3 = 10$ | $a_3 = 10$ |
| $a_4 = 79$ | $a_4 = 67$ |

C. With such schedules available, a homogeneous terpolymer of VP, MAPTAC and ODMA can be prepared as described in Example 2 below.

EXAMPLE 2

Preparation of a Homogeneous Terpolymer of VP, MAPTAC and ODMA

VP (303.6 g), MAPTAC (7.8 g), ODMA (3.1 g), and ethanol (1001.0 g) are charged into a 2-liter resin pot equipped with a gas inlet, a liquid inlet, a thermometer and a condenser. The pH of the solution is adjusted to about 7.5 with KOH. Then a stream of nitrogen is introduced which bubbles through the solution during the reaction. The solution is gradually heated to 65° C. Then MAPTAC (63.2 g) and octadecyl methacrylate (ODMA) (51.4 g) are introduced incrementally into the pot with vigorous stirring over a period of 5 hours so that the relative concentrations of the monomeric VP, MAPTA and ODMA monomer remain practically constant throughout the reaction at predetermined levels.

As soon as MAPTAC and ODMA is introduced to the pot, Lupersol 11 (t-butylperoxy pivalate in mineral spirits) catalyst is added. The rate of the addition of the catalyst is such that 2 ml of Lupersol is completely delivered in 4 hours. The solution is held for an additional 3 hours at the 68° C. The product is an alcoholic solution of the homogeneous terpolymer of VP, MAPTAC and ODMA.

180 g of the polymer solution then was transferred to a 2-liter flask and 500 g of distilled water was added. The resulting solution then was stripped under reduced pressure at 40–50° C. on a rotovap to remove 200 g of solvent (ethanol/water). A clear viscous polymer solution in water was obtained.

The sequence and mode of addition of monomers during the process is summarized in the Table below and the plot in FIG. 2.

TABLE

| HOMOGENEOUS POLYMERIZATION OF VP, MAPTAC AND ODMA | | | | | |
|---|---|---|---|---|---|
| Time (min) | VP (g) | MAPTAC (g) | ODMA (g) | EtOH (g) | Total (g) |
| 0 | 303.6 | 7.8 | 3.1 | 1001.0 | 1315.46 |
| 0–30 | 0 | 13.2 | 10.3 | 0.0 | 1338.93 |
| 30–60 | 0 | 11.9 | 10.3 | 0.0 | 1361.12 |
| 60–90 | 0 | 10.0 | 8.6 | 0.0 | 1379.66 |
| 90–120 | 0 | 8.0 | 6.8 | 0.0 | 1394.48 |
| 120–150 | 0 | 6.3 | 5.1 | 0.0 | 1405.88 |
| 150–180 | 0 | 4.7 | 3.7 | 0.0 | 1414.36 |
| 180–210 | 0 | 3.5 | 2.6 | 0.0 | 1420.50 |
| 210–240 | 0 | 2.5 | 1.8 | 0.0 | 1424.86 |
| 240–270 | 0 | 1.8 | 1.2 | 0.0 | 1427.90 |
| 270–300 | 0 | 1.3 | 0.8 | 0.0 | 1430.00 |
| Total | 303.6 | 71.0 | 54.5 | 1001.0 | 1430.00 |

TABLE-continued

| HOMOGENEOUS POLYMERIZATION OF VP, MAPTAC AND ODMA | | | | | |
|---|---|---|---|---|---|
| Time (min) | VP (g) | MAPTAC (g) | ODMA (g) | EtOH (g) | Total (g) |
| % wt | 21.23 | 4.96 | 3.81 | 70.00 | 100.00 |
| % wt (t = 0) | 23.08 | 0.59 | 0.23 | 76.10 | 100.00 |

HAIR CARE PRODUCT

The homogeneous terpolymer of the invention contains a predetermined dominant blend of a hydrophilic part, i.e. VP/MAPTAC, and a small proportion of a hydrophobic monomer, i.e. RMA. This homogeneous terpolymer composition enables the terpolymer to be readily adsorbed onto the negatively charged hair in high amounts as clear films, and to provide both styling and conditioning functions, while still being capable of being readily rinsed or washed-off with water or shampoo after use.

In use in a water-based, rinse-off, hair styling and conditioning composition, the homogeneous terpolymer of the invention comprises about 0.2–20%, preferably 1–10%, and, most preferably, about 2–8%, by weight of the hair care product, the rest being water, and, optionally including an organic solvent such as ethanol, and/or other acceptable adjuvant components such as silicones, surface active agents, viscosity modifiers, dyes, chelating agents, distributing aids, pearlescent aids, opacifiers, perfumes, fatty alcohols, pH adjusting agents, and the like.

The homogeneous terpolymer of the invention finds particular utility in multifunctional hair care products such as water-based, rinse-off hair styling and conditioning products, and in leave-on hair care products such as a mousse, and may be included as a concentrate, or as a gel, and applied as a self-actuated pump hair spray, or in an aerosol product with a propellant. Various actuator and packaging devices known in the art may be used therewith.

Representative hair care compositions including the homogeneous terpolymer of the invention are given below.

| HAIR CARE COMPOSTION Concentration (% by wt.) | | | |
|---|---|---|---|
| | Suitable | Preferred | Optimum |
| Essential Component | | | |
| Hair Styling and Body Forming Homogeneous Terpolymer* of Invention | 0.2–20 | 1–10 | 4.0 |
| Water | 60–99.8 | 75–85 | 80.4 |
| Optional | | | |
| Surfactant | 0–5 | 0.5–1.0 | 0.6 |
| Organic Solvent | 0–50 | 5–15 | 15 |
| Adjuvants | 0–20 | 0–20 | 0–20 |
| | | | to 100.0 |

| COLORED GEL/MOUSSE | |
|---|---|
| INGREDIENT | % By Weight |
| Homogeneous Terpolymer of Invention | 7.50 |
| Deionized Water | 78.00 |
| Stabileze ® 06 (Crosslinked maleic anhydride- methyl vinyl ether - ISP) | 1.00 |
| Triethanolamine, 98% | 1.00 |
| Sodium Cocoyl Isethionate | 2.50 |
| Color (Pigment) | 4.00 |
| Hydroxylated Lecithin | 1.00 |
| Preservative/Fragrance | qs |
| Propellant A-46 | 5.00 |
| | 100.00 |

Procedure:

1. Charge Stabileze® into 80% of the water requirement, heat to 800° C., maintain mixing 30–40 minutes until translucent.
2. Neutralize with TEA:H$_2$O, 1:1 dilution.
3. Gradually blend in a pre-mix of modified terpolymer of invention and withheld water.
4. Add sodium cocoyl isethionate and blend until homogenous.
5. Add hydroxylated lecithin and blend.
6. Disperse pigment in gel structure until uniform.
7. Add preservative/fragrance sequentially. Mix well.
8. Fill in suitable container and charge with 5% A-46 propellant.

| CONDITIONING/STYLING MOUSSE | |
|---|---|
| INGREDIENT | % By Wt. |
| Homogeneous Terpolymer of Invention | 5.00 |
| Deionized water | 85.90 |
| PVP/VA S-630 | 1.00 |
| Oleth-20 | 0.50 |
| Na$_4$EDTA | 0.10 |
| Fragrance/Preservative | qs |
| n-Butane | 4.50 |
| Difluoroethane | 3.00 |
| | 100.00 |

Procedure:

1. Premix terpolymer of invention with 80% of the water requirement to which tetrasodium EDTA has been added.
2. Prepare a pre-mix of Oleth-20 and fragrance by heating the Oleth-20 to –5° C. above its melting point.
3. Add the PVP/VA S-630 to the modified Gafquat from step 1. Blend until homogeneous.
4. Add the pre-mix of Oleth-20 and fragrance from step 2. Blend until homogeneous.
5. Add preservative and blend.
6. Fill in suitable container and charge with n-butane 4.5% and difluoroethane (3%).

| STYLING GEL-1 | |
|---|---|
| INGREDIENT | % By Wt. |
| Homogeneous Terpolymer of Invention | 5–10 |
| Deionized Water | 85.30 |
| Stabileze ® 06 | 1.00 |
| Na$_4$EDTA | 0.05 |
| Benzophenone-4 | 0.05 |
| NaOH, 10% aqueous | 2.30 |
| Suttocide A, 50% aqueous | 0.30 |
| Oleth-20 | 0.50 |
| Fragrance | qs |
| | 100.00 |

| STYLING GEL-2 | |
|---|---|
| INGREDIENT | % By Wt. |
| Homogeneous Terpolymer of Invention | 7.50 |
| Deionized Water | 87.54 |
| Stabileze ® 06 | 0.70 |
| NA$_4$EDTA | 0.05 |
| Benzophenone-4 | 0.05 |
| Sodium hydroxide, 10% aqueous | 1.66 |
| PVP K-120 | 1.50 |
| Suttocide A, 50% aqueous | 0.30 |
| Oleth-20 | 0.50 |
| Fragrance | 0.20 |
| | 100.00 |

Procedure:

1. Charge Stabileze® into 80% of the water requirement. Heat to 80° C., hold at 80° C. for 30 minutes or until translucent.
2. Add NaOH, 10% aqueous and blend until a clear gel is formed.
3. Add Na$_4$EDTA and blend.
4. Pre-mix benzophenone-4 with a small amount of withheld H$_2$O and add to the gel. Blend until homogeneous.
5. Pre-dissolve PVP K-120 in approximately 10 times its weight of water. Slowly add to the gel structure and blend until homogeneous.
6. Pre-mix terpolymer of invention with the remaining withheld water and blend into the gel structure until homogeneous.
7. Pre-heat Oleth-20 until it melts and form and pre-mix with the fragrance.
8. Blend into the gel structure till clear.

While the invention has been described with particular reference to certain embodiments thereof, it will be understood that changes and modifications may be made which are within the skill of the art. Accordingly, it is intended to be bound only by the following claims, in which:

What is claimed is:

1. A water-based, multifunctional hair care product having both hair styling and conditioning properties which includes 0.2–20% by weight of a homogeneous terpolymer of predetermined composition comprising, by weight, (a) about 55–99% of a vinyl lactam monomer, (b) about 0.5–49% of a quaternary amino acrylamide or acrylate monomer, methacrylamide or methacrylate monomer, or mixture thereof, and (c) about 0.5–49% of a hydrophobic monomer defined by RMA where R is a C$_4$–C$_{32}$ alkyl and MA is an acrylate, methacrylate, acrylamide or methacrylamide.

2. A hair care product including the homogeneous terpolymer of claim 1 wherein (a) is vinyl pyrrolidone.

3. A hair care product including the homogeneous terpolymer of claim 1 wherein (b) has the formula:

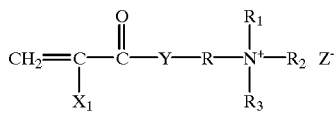

where
Y is O or —NX—,
R is $C_2$–$C_{20}$ alkyl or

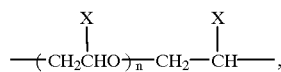

where n is 0–10,
X and $X_1$ are independently H, $C_1$ to $CH_8$ alkyl,
$R_1$, $R_2$ and $R_3$ are independently $C_1$–$C_4$ alkyl, and
Z is a halide, sulfate or sulfonate.

4. A hair care product including the homogeneous terpolymer of claim 1 wherein (c) has the formula RMA where R is $C_4$–$C_{32}$ alkyl, and MA is an acrylate or methacrylate.

5. A hair care product including the homogeneous terpolymer of claim 1 comprising (a) about 65–95% by weight of vinyl pyrrolidone, (b) about 0.5–40% by weight of (3-methacrylamidopropyl) trimethylammonium chloride, and (c) about 0.5–15% by weight of octadecyl methacrylate.

6. A hair care product including the terpolymer of claim 2 wherein (a) is 70–95%; (b) is 5–15%; and (c) is 1–10%.

7. A hair care product including the homogeneous terpolymer of claim 1 wherein (a) is vinyl pyrrolidone, (b) is a quaternary salt of an aminoacrylamide or acrylate, methacrylamide, methacrylate, and (c) is a hydrophobic alkylacrylate, methacrylate, alkylacrylamide or methacrylamide.

8. A hair care product including the homogeneous terpolymer of claim 1 wherein (a) is vinyl pyrrolidone, (b) is a quaternized amino acrylamide, and (c) is a $C_4$–$C_{32}$ alkyl methacrylate.

9. A hair care product including the homogeneous terpolymer of claim 1 wherein (a) is vinyl pyrrolidone, (b) is (3-methacrylamidopropyl) trimethyl ammonium chloride, and (c) is octadecyl methacrylate.

10. A hair care product according to claim 1 which also includes a propellant.

11. A hair care product according to claim 1 which includes about 1–10% by weight of said homogeneous terpolymer.

12. A hair care product according to claim 11 which includes about 2–8% by weight of said homogeneous terpolymer.

13. A hair care product according to claim 1 in the form of a gel, lotion, mousse or glaze.

14. A hair care product according to claim 1 which includes about 60–95% of water, 0–5% of a surfactant and 0–50% of an organic solvent.

* * * * *